United States Patent
Strauss et al.

(10) Patent No.: US 9,186,199 B2
(45) Date of Patent: Nov. 17, 2015

(54) HIGH FREQUENCY SURGERY APPARATUS AND METHOD OF OPERATING SAME

(75) Inventors: Timo Strauss, Berlin (DE); Godo Strauss, Unterschleissheim (DE); Uwe Fischer, Berlin (DE)

(73) Assignee: OLYMPUS WINTER & IBE GMBH (DE)

(*) Notice: Subject to any disclaimer, the term of this patent is extended or adjusted under 35 U.S.C. 154(b) by 1507 days.

(21) Appl. No.: 12/669,501

(22) PCT Filed: Jul. 17, 2008

(86) PCT No.: PCT/EP2008/059398
§ 371 (c)(1),
(2), (4) Date: Jan. 18, 2010

(87) PCT Pub. No.: WO2009/010565
PCT Pub. Date: Jan. 22, 2009

(65) Prior Publication Data
US 2010/0198217 A1    Aug. 5, 2010

(30) Foreign Application Priority Data
Jul. 19, 2007 (DE) .......................... 10 2007 034 271

(51) Int. Cl.
A61B 18/12  (2006.01)
A61B 18/00  (2006.01)

(52) U.S. Cl.
CPC .... *A61B 18/1206* (2013.01); *A61B 2018/00702* (2013.01); *A61B 2018/00857* (2013.01); *A61B 2018/1213* (2013.01)

(58) Field of Classification Search
CPC ................. A61B 18/1206; A61B 2018/00702; A61B 2018/00857; A61B 2018/1213
USPC .......................................... 606/32, 34, 37–40
See application file for complete search history.

(56) References Cited

U.S. PATENT DOCUMENTS 4,114,623 A * 9/1978 Meinke et al. ................... 606/39
4,209,018 A * 6/1980 Meinke et al. ................... 606/40
4,860,745 A   8/1989 Farin et al.
(Continued)

FOREIGN PATENT DOCUMENTS

DE    25 04 280    8/1976
DE    41 26 607    2/1993
(Continued)

*Primary Examiner* — Michael Peffley
*Assistant Examiner* — Samantha Good
(74) *Attorney, Agent, or Firm* — Ostrolenk Faber LLP

(57) ABSTRACT

The invention concerns a high frequency surgery apparatus for cutting and/or coagulating biological tissue and methods of operating same. The high frequency surgery apparatus includes at least one high frequency generator which in operation forms a high frequency circuit with the tissue to be treated, with the production of an arc, and at least one measuring and calculating device which is connected for signal transmission to the high frequency circuit and which is adapted in operation to ascertain both a DC voltage in the high frequency circuit and also the amplitudes of at least one even and at least one odd harmonic of a fundamental frequency of the high frequency generator and to form a first tissue parameter representative of the kind of tissue to be treated from the relationship of the sum of the amplitudes of the even and the odd harmonics to the DC voltage and to output a tissue signal dependent on the first tissue parameter for subsequent processing.

17 Claims, 10 Drawing Sheets

(56) References Cited

U.S. PATENT DOCUMENTS

| | | | |
|---|---|---|---|
| 5,749,869 A * | 5/1998 | Lindenmeier et al. | 606/34 |
| 2003/0158546 A1 * | 8/2003 | Farin et al. | 606/34 |
| 2005/0137589 A1 | 6/2005 | Daners et al. | |

FOREIGN PATENT DOCUMENTS

| | | |
|---|---|---|
| DE | 195 42 418 | 5/1997 |
| DE | 195 42 419 | 5/1997 |
| JP | 63-024933 | 2/1988 |
| JP | 2006-506129 | 2/2006 |
| JP | 2006-289061 | 10/2006 |
| WO | WO 93/03677 | 3/1993 |
| WO | WO 03/090634 | 11/2003 |
| WO | WO 2006-050888 | 5/2006 |

* cited by examiner

HIGH FREQUENCY SURGERY APPARATUS AND METHOD OF OPERATING SAME

CROSS-REFERENCE TO RELATED APPLICATIONS

The present application is a 35 U.S.C. §§371 national phase conversion of PCT/EP2008/059398, filed Jul. 17, 2008, which claims priority of German Patent Application No. 10 2007 034 271.5, filed Jul. 19, 2007. The PCT International Application was published in the English language.

BACKGROUND OF THE INVENTION

The invention concerns a high frequency surgery apparatus for cutting and/or coagulating biological tissue comprising at least one high frequency generator which in operation forms a high frequency circuit with the tissue to be treated with the formation of an arc.

The invention further concerns a method of operating a high frequency surgery apparatus, wherein for cutting and/or coagulating biological tissue a high frequency circuit is formed between at least one high frequency generator and the tissue to be treated, with the formation of an arc.

The term high frequency surgery is used essentially to denote cutting and coagulating (sclerosing) biological tissue using high frequency currents (about 0.2 MHz to 3 MHz). In that respect the cutting effect in biological tissue is based on the formation of an arc between an active electrode and the tissue. To achieve a cut which is as uniform as possible, with constant haemostasis (cutting result) the arc parameters are used as a regulating criterion for the high frequency generator.

In coagulation the high frequency current is used for haemostasis or for the ablation of tissue. In that case the tissue surrounding the electrode is heated by the current to such an extent that body-specific albumins break down and stick together and intracellular as well as extracellular fluids vaporise. That results in denaturing and shrinkage of the tissue and the blood vessels and thus ultimately stopping of hemorrhages. In ablation a tissue region which is to be destroyed or removed from the body is denatured in that way. The tissue region treated in that way heals up and is broken up by body-specific processes without having to be removed by an operative procedure.

In the cutting operation arcs are produced through a vapour layer of cell fluid between a cutting electrode and the tissue. The point concentration of the high frequency current in the arc gives rise to a flash-like increase in the temperature of the cellular tissue, which leads to abrupt vaporisation of the cell fluid and ultimately cell explosion. The cutting effect occurs due to the distribution of the arcs as they ignite over the active electrode, wherever the vapour layer between the tissue and the electrode is sufficiently thin. In that case electrically conductive tissue can be severed virtually without mechanical pressure. Due to the high temperatures the risk of germs being spread is reduced, in addition at the same time it is possible to achieve coagulation of surrounding pieces of tissue.

The monopolar procedure involves the use of an active coagulation or cutting electrode and a neutral electrode which is applied over a large area. In that case the high frequency current flows from the active electrode to the neutral electrode by way of the tissue to be treated. The crucial consideration for the thermal action of the current at the application placement is an active electrode of small area, in relation to a neutral electrode of large area. That provides for a high current density and thus a substantial increase in the temperature of the tissue at the operation location and at the same time avoids unwanted tissue damage at the neutral electrode.

Bipolar applications involve the use of two evenly matched electrodes which are combined in one instrument. In that case the high frequency current flows from the one electrode of the surgical instrument to the other electrode thereof by way of the tissue to be treated. Alternatively the electrodes can also be provided on different units. The best-known instruments in that respect are coagulation forceps with which blood vessels can be specifically and targetedly gripped and then closed.

In the present document the arc intensity is defined as a measurement in respect of the frequency of occurrence and the number of ignited arcs. It is proportional to the power which is converted at the arc for spark flash-over and for maintaining the vapour layer. With a constant power delivery from the HF generator arc intensity depends on parameters such as cutting depth, cutting speed and tissue factors. Regulation of the arc intensity is used to achieve cutting results which as far as possible are independent of the tissue factors and cutting parameters. In that respect the term cutting result is used to denote the degree of coagulation (desired) and the degree of carbonisation (carbonisation: unwanted material or tissue carbonisation) of the cut surfaces.

Biological tissue is not a homogeneous mass. Muscle, fat and other kinds of tissue as well as blood vessels alternate. The speed and the depth of penetration of the electrode also change during the cutting operation. As a result the electrical conditions under which the cutting electrode is guided are constantly changing. HF generators without arc regulation cannot adapt their electrical output parameters to those variable use conditions. In the case of a cutting operation the active electrode is surrounded by a film of vaporised cell fluid. The vapour layer is compressed and displaced by virtue of the advance movement in the region in front of the electrode. It is there that the arcs are ignited in the case of an optimum cutting operation due to the thinner vapour layer. With an excessively high power output from the HF generator the arcs are ignited distributed over the entire electrode surface.

The desired result in the case of a cut made with an HF surgery apparatus is tissue separation in which the cut surfaces are coagulated but not carbonised. An excessively high power delivery from the HF generator does not lead to an improved cutting result but an increased level of arc intensity. That involves more severe necrosis and carbonisation of the cut surfaces. That delays the healing process and is therefore absolutely to be avoided. In contrast if the power is too low an arc can no longer be ignited and the cutting operation comes to a halt.

Commercially available HF generators regulate the output voltage of the generator to keep the arc intensity between the cutting electrode and the tissue constant. With that regulating system the output power of the HF generator can be substantially better adapted to the prevailing operative requirements than with constant voltage regulation or completely without regulation. In the case of an ideal HF surgery apparatus the cutting result would always be constant and reproducible under all conditions. It is here that previously technically implemented arc regulating systems meet their limits for there is a marked residual dependency in respect of the degree of coagulation and carbonisation of the cut surfaces for example on the cutting speed and the cutting depth.

Technical recognition of the tissue in which the operator is cutting considerably increases the level of certainty when using HF surgery. In the ideal case the surgery apparatus should detect the kind of tissue in which the operation is to be carried out and should shut down or react with signalling as soon as the cutting electrode comes into contact with other pieces of tissue in order to avoid unwanted damage thereto.

High frequency surgery apparatuses and methods of operating same are known from the state of the art.

DE 25 04 280 describes for example an apparatus for cutting and coagulating human tissue with high frequency current, which is regulated on the basis of the state of the cutting or coagulating procedure.

Detecting arc intensity for controlling a high frequency generator is set forth in DE 195 42 418.

A high frequency generator with tissue differentiation on the basis of a current-voltage characteristic measured at a high frequency generator is described in DE 195 42 419.

DE 28 01 833 shows an electrosurgical cutting apparatus in which a regulator for the HF voltage of the HF generator responds to a DC voltage which is produced in the cutting operation.

DE 41 26 607 describes an arrangement for cutting biological tissue with high frequency current.

The problem with the known high frequency surgery apparatuses and the control methods thereof is that different cutting results can occur because there is a dependency on the parameters determined by the operator such as for example cutting speed and cutting depth and the kind of tissue, such as for example muscle tissue or fat tissue.

SUMMARY OF THE INVENTION

Therefore the object of the present invention is to provide a high frequency surgery apparatus and a method of operating same, which gives improved cutting results in comparison with the state of the art.

That object is attained by the high frequency surgery apparatus and the method of operating same as set forth in the independent claims.

The high frequency surgery apparatus according to the invention attains the object by the formation of a first tissue parameter representative of the kind of tissue. The first tissue parameter is calculated from the relationship of the sum of the amplitudes of the even and the odd harmonics of a fundamental frequency of the high frequency generator to the DC voltage in the high frequency circuit. Tests have shown that that tissue parameter reflects the kind of tissue and at the same time is independent of the cutting speed determined by the operator. Therefore that first tissue parameter can be used for example for automatic regulation of the output value of the high frequency generator such as the output power or the output voltage.

The other high frequency surgery apparatus according to the invention attains the above-specified object by determining a speed parameter representative of the cutting speed. That speed parameter is calculated from a quotient from the DC voltage in the high frequency circuit and the amplitude of the harmonic of a fundamental frequency of the high frequency generator and/or from a quotient from the DC voltage and the output current. Tests have shown in that respect that the speed parameter reflects the cutting speed with which the operator performs the cut. Consequently the speed parameter according to the invention can be used for example to automatically adapt the output value of the high frequency generator to the cutting speed. That regulation provides for a uniform cutting result.

Further advantageous configurations of the invention are described in the appendant claims.

Thus the high frequency surgery apparatus can have at least one control device connected to the measuring and calculating device for controlling or regulating an output value of the high frequency generator, wherein the control device is adapted to control or regulate the output value on the basis of the tissue signal and/or the speed signal. That has the advantage that automatic regulation of the output value such as the output voltage or the output power of the HF generator is possible, with a uniform cutting quality, independently of the cutting speed and/or the kind of tissue.

BRIEF DESCRIPTION OF THE DRAWINGS

The invention is described in greater detail hereinafter with reference to the accompanying Figures in which.

DETAILED DESCRIPTION

Figure 1:
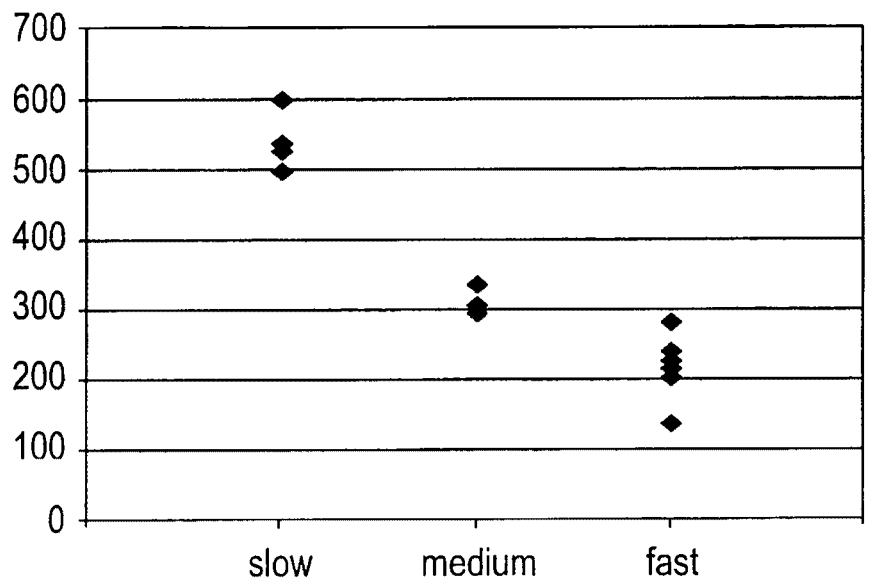
FIG. 1 shows a view of the quotient of UDC/I in the case of cuts at varying speeds and with a constant output voltage (U=300V), with UDC being a DC voltage and I an output current.

The investigations in connection with the present invention and the invention in embodiments by way of example are described hereinafter.

Detection of the arc by a measurement procedure is the basis of regulation of modern HF generators 2. Some possible ways of detecting various characteristic parameters of the arc are described hereinafter.

Harmonics in the Frequency Spectrum

Evaluation of the frequency spectrum of the current when cutting tissue 5 is known. Due to the non-linear characteristic of the arc flash-over, harmonics occur in the frequency spectrum of the output current of the HF generator 2. The degree to which the current configuration is deformed and deviates from the basic sine shape depends on the intensity of the arc flash-over. Accordingly the harmonic content is proportional to the arc intensity and can be used as a criterion for regulating the output power. Generators in which under load the output voltage differs greatly from the sine form (voltage breakdown) produce a corresponding frequency spectrum also for the output voltage.

DC Voltage

In the case of monopolar cutting in HF surgery the arc burns between a metallic electrode 7 and tissue 5. By virtue of the differing work function which the charged particles must produce at the greatly different materials the arc has a rectification effect similarly to a metal semiconductor diode. It is only in the event of an arc flash-over that a DC voltage (DC component) occurs. That DC voltage can be measured at the capacitor 12 which serves for blocking off direct currents in the patient circuit. It is with limitations proportional to the arc intensity and can be utilised for regulating the HF generator 2. Arc regulation in the case of known HF surgery apparatuses 1 is based for example on detection of the DC voltage upon arc flash-over.

Amplitudes of the Harmonics in the Frequency Spectrum of the Current

The frequency spectrum of the current can be used as a feature for differentiating tissue 5. Tests have shown that the frequency spectrum is dependent on the electrode materials. When cutting with a high frequency surgery apparatus 1 the material of the active cutting electrode 7 which is guided by the surgeon 9 does not change. Therefore, by evaluating the amplitudes of the individual harmonics, it is possible to provide information about the material surrounding the cutting electrode 7. Therefore the relationship between the amplitudes of the even and odd harmonics can be utilised for evaluation purposes. Tests have shown that for example the relationship of the amplitudes of the second to the third harmonics in muscle tissue differs from the relationship of the amplitudes of the same harmonics in fat tissue.

Test Result for Detecting Electrode Speed

The resistance of the electrode-tissue arrangement decreases with increasing speed. That relationship can be explained on the basis of the model representation that the active electrode 7 is surrounded by a sheathing of vaporised cell fluid during the cutting operation. That vapour layer is compressed in the advance direction so that the arcs ignite at that location due to the thinner vapour layer. If now the advance speed is increased and the vapour layer therefore becomes more greatly compressed and thinner, its resistance also decreases. As, with a constantly regulated DC voltage UDC the degree of coagulation of the cut surfaces decreases with an increasing cutting speed, an additional parameter is required, with which the advance speed of the electrode 7 is taken into consideration to a greater extent than with the DC voltage UDC alone. The output current I of the HF generator 2 presents itself for that purpose.

By forming the relationship between the DC voltage UDC and the current I, that gives a value in which both the tissue influence is taken into account (by means of UDC) and also the influence of the cutting speed is taken into account (by means of I), as shown in FIG. 1.

Figure 2:
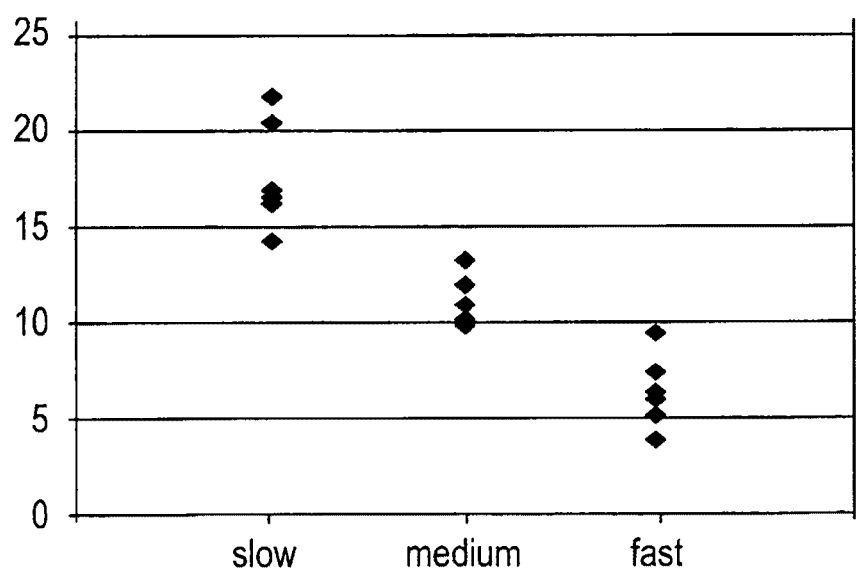
FIG. 2 shows a view of the quotient of UDC/ûf2 in the case of cuts at varying speeds and with a constant output voltage (U=300V), with ûf2 being the peak voltage/voltage amplitude at the frequency f2, which is the frequency of even harmonics, e.g., of the second harmonic.

In addition there is a similar connection in regard to the relationship between the DC voltage UDC and the amplitude of the second harmonic in the frequency spectrum of the output voltage $\hat{u}f2$, as shown in FIG. 2.

Test Result for Detecting the Frequency Spectra

Tests have shown that there is a strong dependency in respect of the harmonics on the cutting speed. The electrode or cutting speed depends on the operator 9 who is guiding the electrode 7 through the tissue 5. The result of technical tissue differentiation however should not be capable of being influenced by the user (operator) 9. Therefore, for tissue differentiation, it is necessary to find a parameter which is not speed-dependent and which therefore cannot be influenced by the operator 9.

Figure 3:
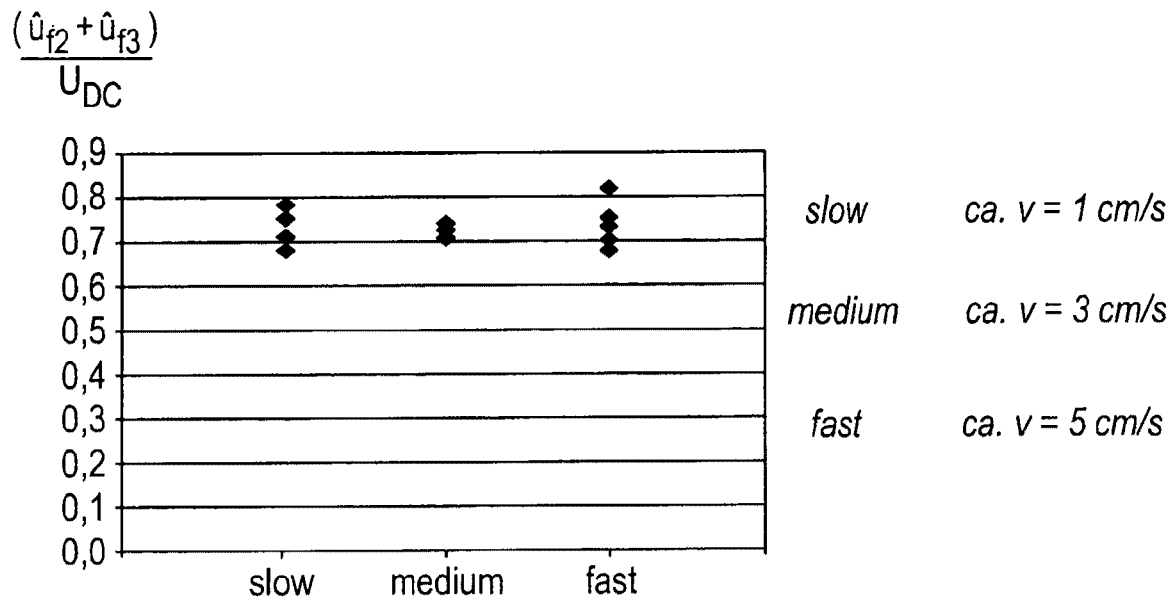
FIG. 3 shows a variation in the parameter (ûf2+ûf3)/UDC in the case of a plurality of cuts at different speeds (U=const.=300V), with ûf3 being the peak voltage/voltage amplitude at the frequency f3, which is the frequency of odd harmonics, e.g., of the third harmonic.
Figure 4:
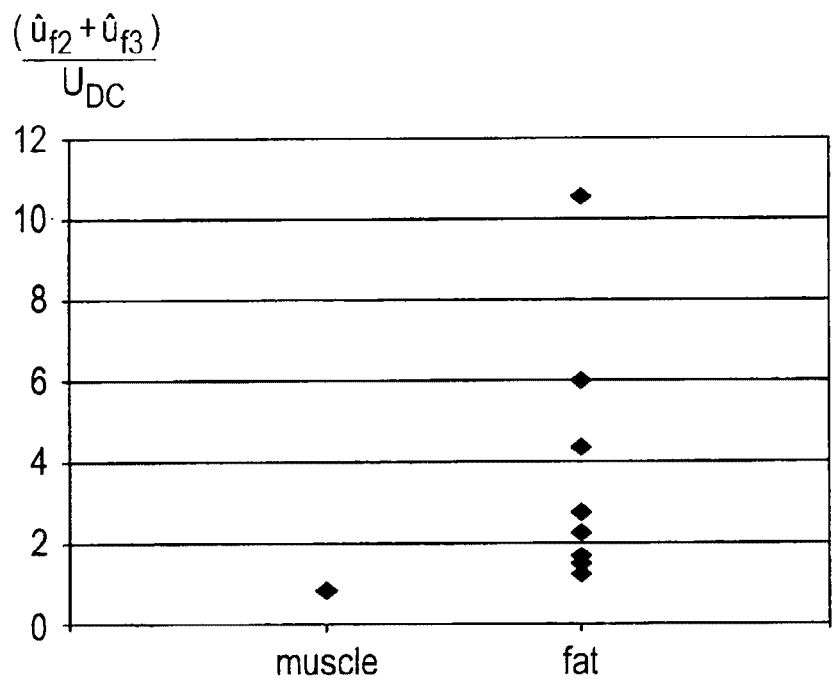
FIG. 4 shows a variation in the parameter ascertained by calculation (ûf2+ûf3)/UDC in the case of a plurality of cuts through muscle and fat tissue (U=const.=300V)

FIG. 3 shows that the parameter $(\hat{u}f2+\hat{u}f3)/UDC$ which is ascertained by calculation is not dependent on the electrode speed. FIG. 4 shows that that parameter $(\hat{u}f2+\hat{u}f3)/UDC$ is dependent on the kind of tissue 5 through which the active electrode 7 is being guided. The parameter $(\hat{u}f2+\hat{u}f3)/UDC$ can therefore also be referred to as a first tissue parameter.

The first tissue parameter $(\hat{u}f2+\hat{u}f3)/UDC$ according to the invention allows speed-independent differentiation of tissue materials. In order to further increase the options for distinguishing different kinds of tissue 5 it is also possible to add additional measurement values such as for example the overall effective value of the output voltage to the first parameter.

Evaluation of the Output Voltage

Figure 5:
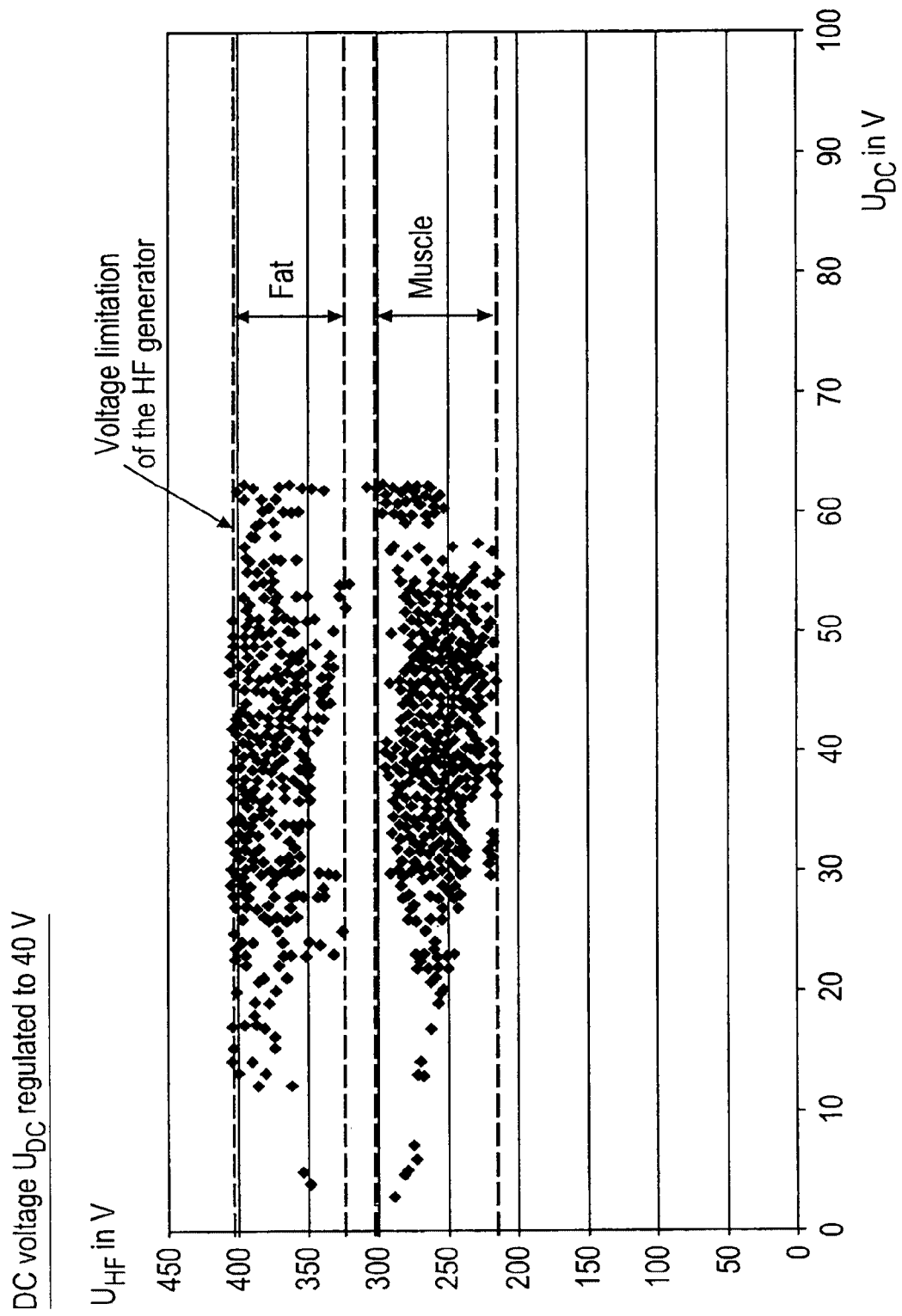
FIG. 5 shows an output voltage UHF over DC voltage UDC in the case of a plurality of cuts through muscle and fat tissue with arc regulation (DC voltage UDC produced by arc regulated at 40V)

FIG. 5 shows a diagram illustrating measurement values of the output voltage, wherein the DC voltage was regulated to 40V for tissue differentiation. Given data ranges in the transitional region between muscle tissue and fat tissue were cut out in data evaluation in order to obtain an informative diagram in which it is possible to distinguish muscle tissue and fat tissue. Arc regulation cannot abruptly adapt the output voltage UHF to the tissue factors. That gives rise to a transitional region in which no information about the kind of tissue 5 can be afforded.

Test Result for Evaluation of the Output Voltage

When making a cut from muscle to fat tissue arc regulation of an HF regulator in the state of the art adapts the output voltage UHF to the tissue in order to keep the arc intensity (detected by means of the DC voltage UDC) substantially constant. FIG. 5 shows that tissue distinction is possible on the basis of the output voltage in dependence on the DC voltage (UHF/UDC). Combination with one or more other parameters for reliable tissue differentiation is therefore appropriate.

Detection of the Arc in the State of the Art

Figure 6:
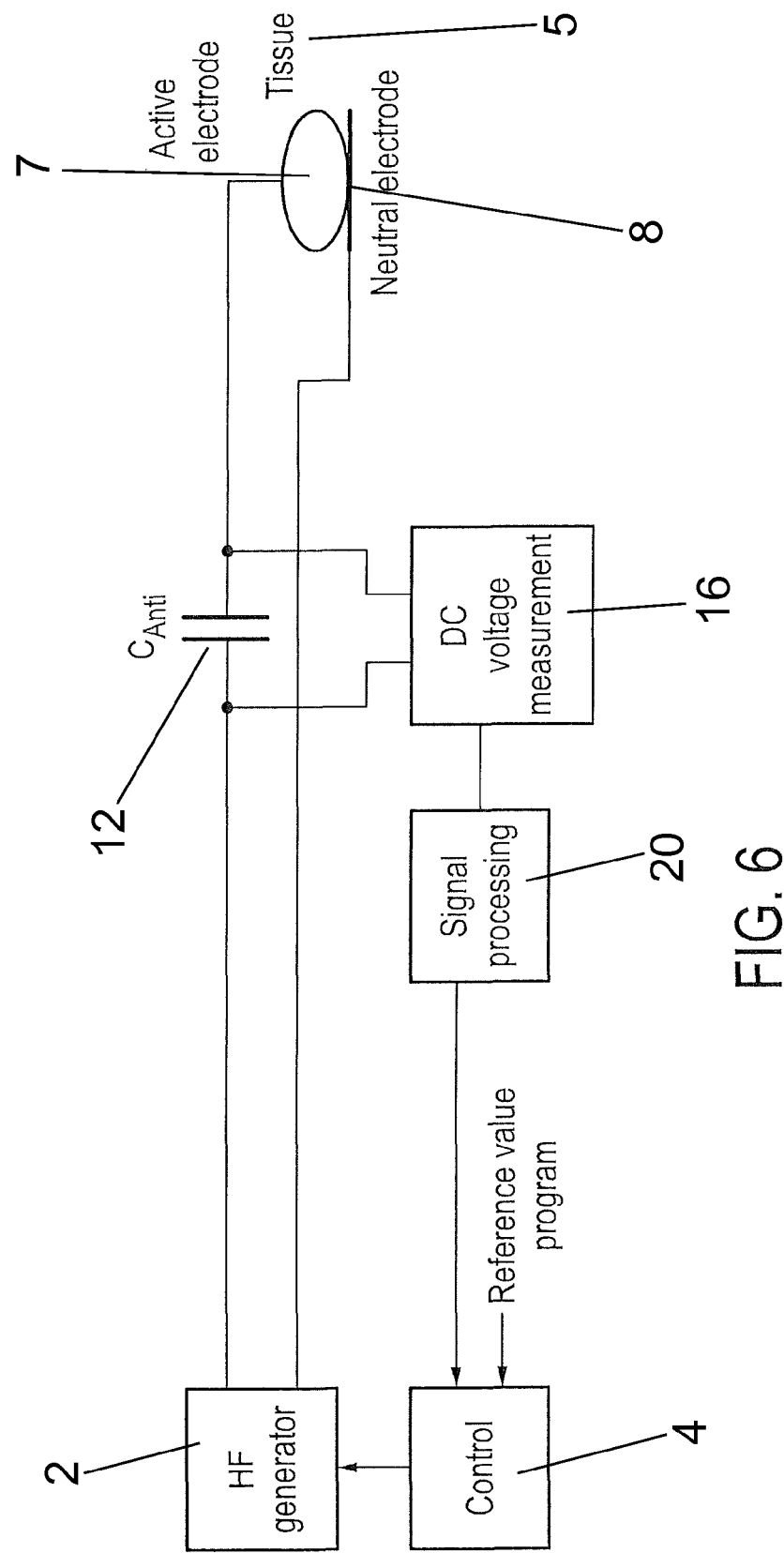
FIG. 6 shows a diagrammatic view of measurement of the DC voltage component.

FIG. 6 shows the principle in the state of the art which is based on the detection of the arc intensity by measurement of the DC voltage across the antifaradisation capacitor CAnti 12 (see illustration 52) in the patient circuit. The arc sensor 14 (see FIG. 11) shown in FIG. 6 is composed of a measurement circuit 16, a PIC-18 microcontroller 4 with the associated peripherals 20 and the interface for data transfer 22 (see FIG. 11). The DC voltage across the capacitor CAnti 12 is detected by means of the A/D-converter 38 (see FIGS. 9 and 10) of the PIC-18 microcontroller 4. It produces from the measurement values the data protocol which is communicated to the CPU of the HF generator 2. The CPU of the HF generator 2 performs the regulating tasks so that an arc-regulated cut can be implemented. The arc sensor 14 itself does not have any tasks in relation to regulation technology, it generates a signal which is proportional to the arc intensity and which is made available to the CPU of the HF generator 2.

Evaluation of the Harmonics in the Frequency Spectrum of the Current

Figure 7:
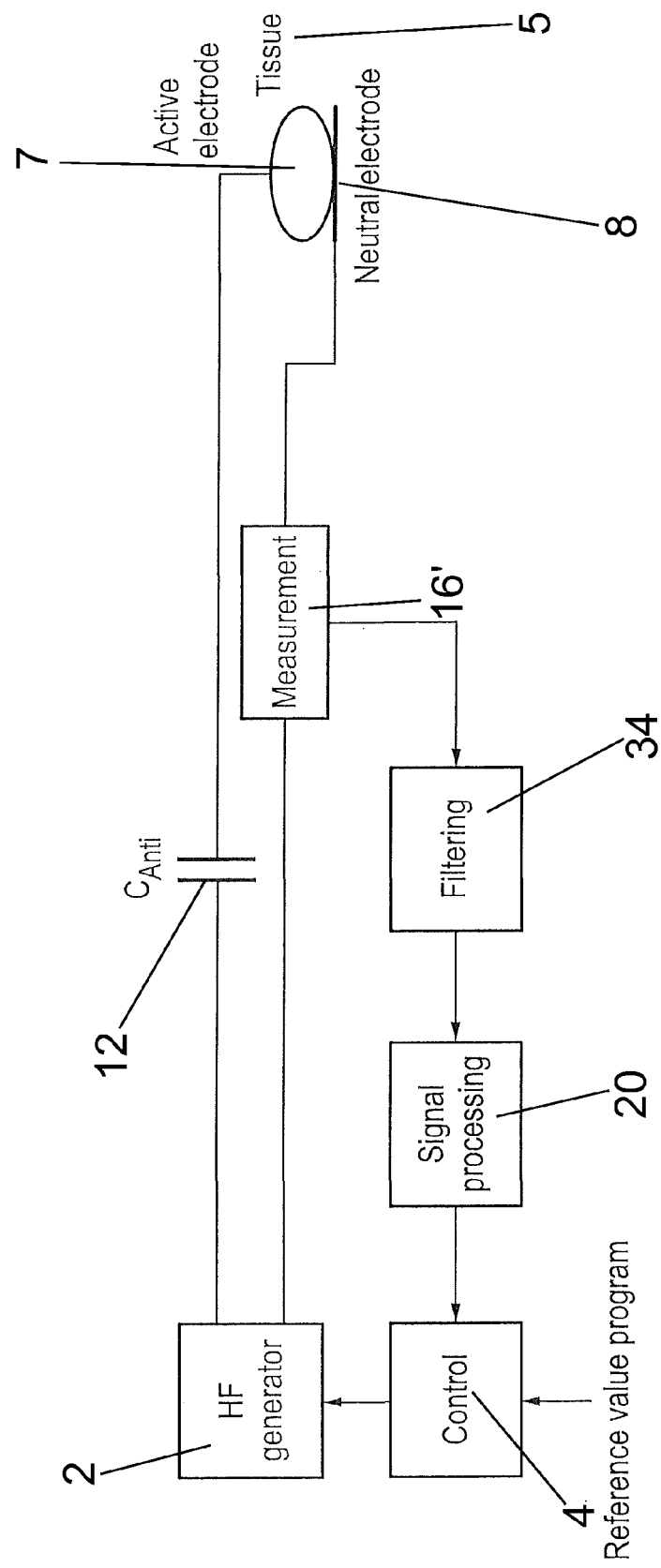
FIG. 7 shows a diagrammatic view of filtering and measurement of the harmonic content.

Evaluation of the harmonics in the frequency spectrum of the current of an HF generator 2 is shown in FIG. 7. As described hereinbefore evaluation of the frequency spectrum both of the current and also of the voltage is basically suitable for detection of the arc intensity. On the basis of tests, it has been possible to demonstrate a connection between arc intensity, cutting speed and cutting result. Furthermore the tests have shown that, to implement such regulation, not just the relationship between arc intensity and current but also the relationship between arc intensity and amplitude of the second harmonic in the frequency spectrum of the output voltage is appropriate.

Evaluation of the Harmonics of the Output Signal

Figure 8:
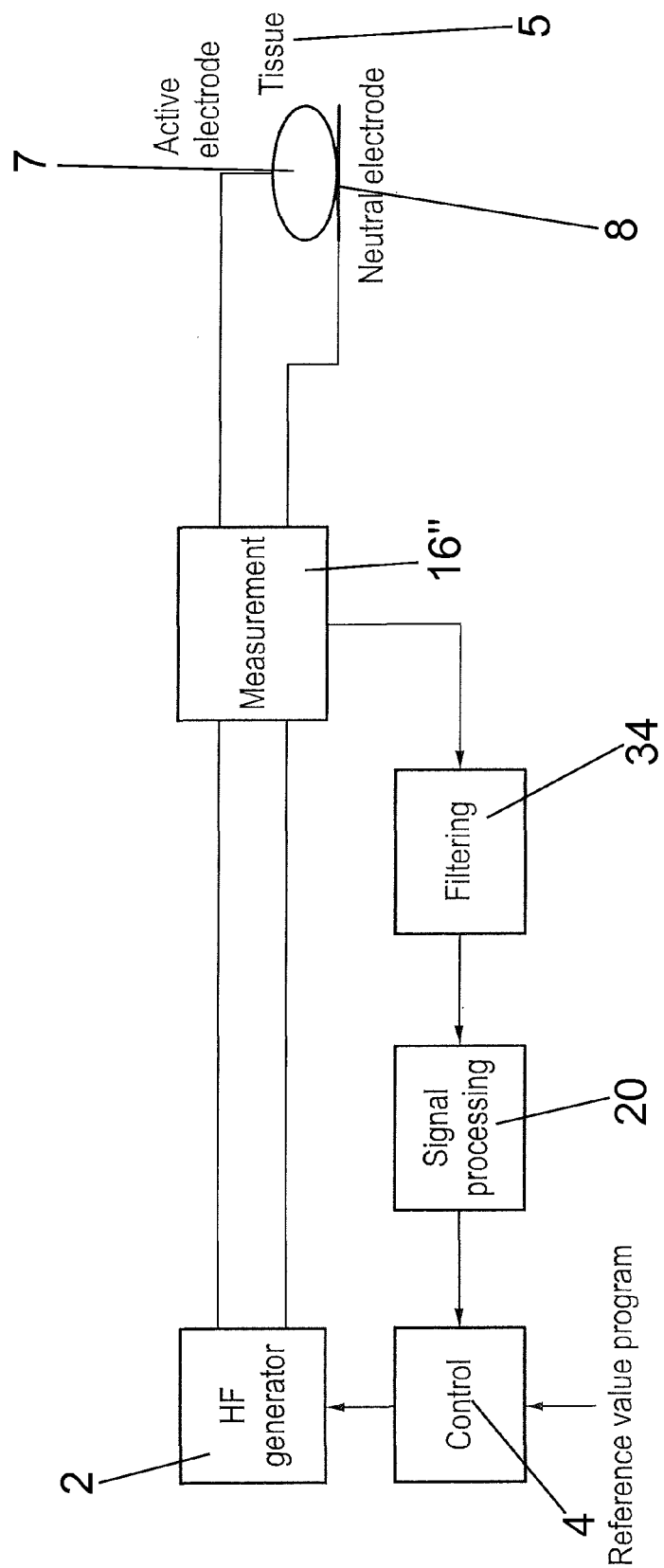
FIG. 8 shows a diagrammatic view of an HF generator with evaluation of the harmonics for tissue differentiation.

Evaluation of the harmonics in the output signal of the HF generator 2 is embodied in the circuit shown in FIG. 8. So that evaluation of the harmonic content is possible the desired frequencies have to be filtered out. In that case the fundamental wave as well as the second and third harmonics are particularly preferred as the amplitude of the higher harmonics decreases and thus differentiation from background noise becomes more difficult.

When cutting into tissue 5 the active electrode 7 is surrounded by a vapour layer so that there is no direct tissue contact. The resistance of the vapour layer and the tissue 5 is in the range of 1 kΩ to 2 kΩ and is thus relatively constant. The frequency of the fundamental wave varies in that case in the range of 330-335 kHz, that of the second harmonic is in the range of 660-670 kHz and that of the third harmonic is in the range of 990-1005 kHz. Accordingly it is possible to dispense with an extremely wide configuration in respect of the band passes for filtering the individual harmonics in an embodiment of the invention. On the basis of the tests it was possible to obtain from the combination of the harmonics with the DC voltage, the tissue-dependent and speed-independent parameter (($\hat{u}f2+\hat{u}f3$)/UDC) with which tissue differentiation is possible.

The relationship between output voltage and DC voltage (UHF/UDC) has also proven to be a further suitable parameter for tissue differentiation. It can therefore be referred to as a second tissue parameter. Evaluation of one or both parameters is therefore appropriate. The risk of faulty tissue identification can be additionally minimised by the combination of two parameters.

Method of Detecting the Arc Parameters

Use of the parameters ascertained in the tests for detection of arc intensity and tissue differentiation for technical implementation thereof is described hereinafter.

In regard to tissue differentiation, both evaluation of the DC voltage and also evaluation of the second and third harmonics in the frequency spectrum of the output voltage is necessary. The two are integrated in an embodiment of the invention. That leads to improved arc regulation for further improving the cutting results, as described hereinafter.

Improving the Cutting Result by a Reduction in the Influence of the Electrode Speed The aim of arc regulation is to obtain a defined cutting result which is always the same and which is independent of the cutting parameters. The desired quality of the cut is preset by the operator by way of the user interface of the HF generator 2. Accordingly the operator 9 fixes the intensity of the arc. Arc intensity is detected by measurement technology and is kept constant at that level by way of a regulating system. With that kind of regulation it is possible for the cutting result to be kept substantially independent of tissue factors. There still remains however a dependency in respect of the cutting result on the cutting speed, that is to say the electrode speed. It has been found that the influence of the cutting speed can be compensated if the arc intensity behaves approximately like the current. That can be achieved by the relationship of the two values being regulated at a constant level. Such regulation (UDC/I) makes it possible to achieve cutting results which are substantially more independent of the cutting speed than in the case of cuts with a constant arc intensity. The test results have shown that implementation of that regulation is also possible by way of evaluation of the second harmonic in the frequency spectrum of the output voltage (UDC/$\hat{u}f2$). That is supplemented with tissue differentiation on the basis of the voltage frequency spectrum and can thus be embodied in a joint sensor.

Filter Design

Figure 9:
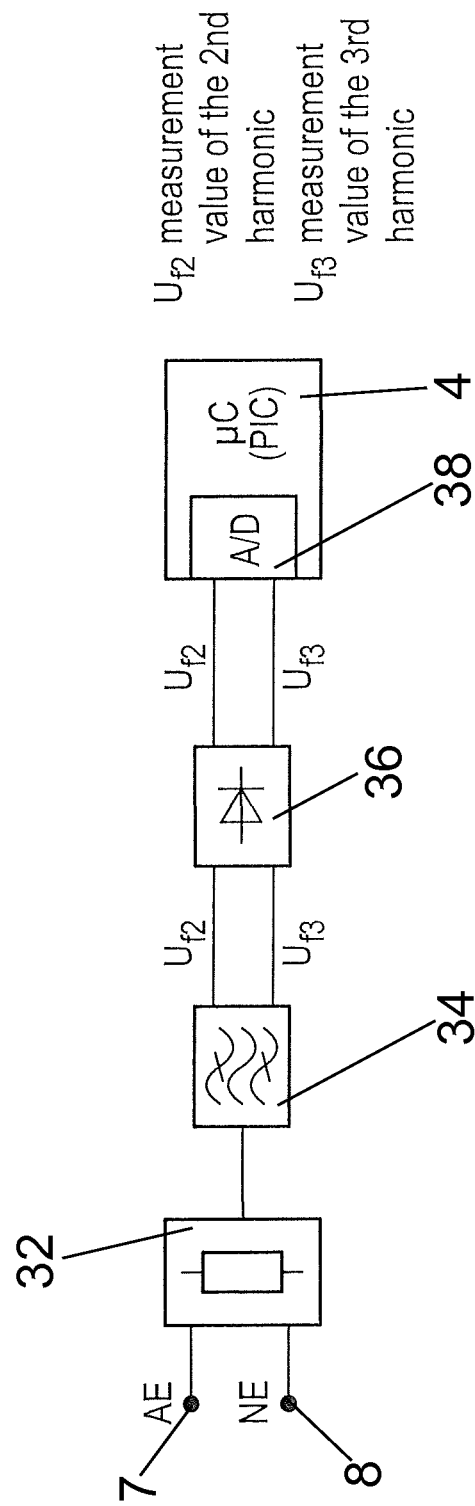
FIG. 9 shows a diagrammatic sketch for evaluation of the second and third harmonics in the voltage spectrum.

Set out hereinafter is also a filter hardware by way of example, with which the second and third harmonics of the voltage frequency spectrum can be evaluated for arc regulation and tissue differentiation, see FIG. 9 and FIG. 10.

The voltage between the active electrode (AE) 7 and the neutral electrode (NE) 8 is divided to the required value by way of a resistor network 32. To generate electrical signals which are proportional to the second and third harmonics in the frequency spectrum of the voltage they can be coupled out of the frequency spectrum using suitable filter technology 34. The output signal of the filters 34 is then actively rectified ('superdiode') 36 and then detected by way of the 10-bit A/D-converters 38 of a PIC-18 microcontroller 4. For reasons of interference insensitivity for example active analog filters 34 are used for implementing the filter technology 34. In particular band pass filters 34 with multiple negative feedback are appropriate for that purpose. The filters 34 are to be operated at a voltage supply of +9V and the maximum output voltage of the filters 34 $\hat{u}$out should be 4V (maximum input voltage of the A/D converters 38). The filter 34 by way of example for the second harmonic should be dimensioned for a transmission range of 660-670 kHz while the filter 34 by way of example for the third harmonic should be dimensioned for the transmission range of 990-1005 kHz.

Figure 10:
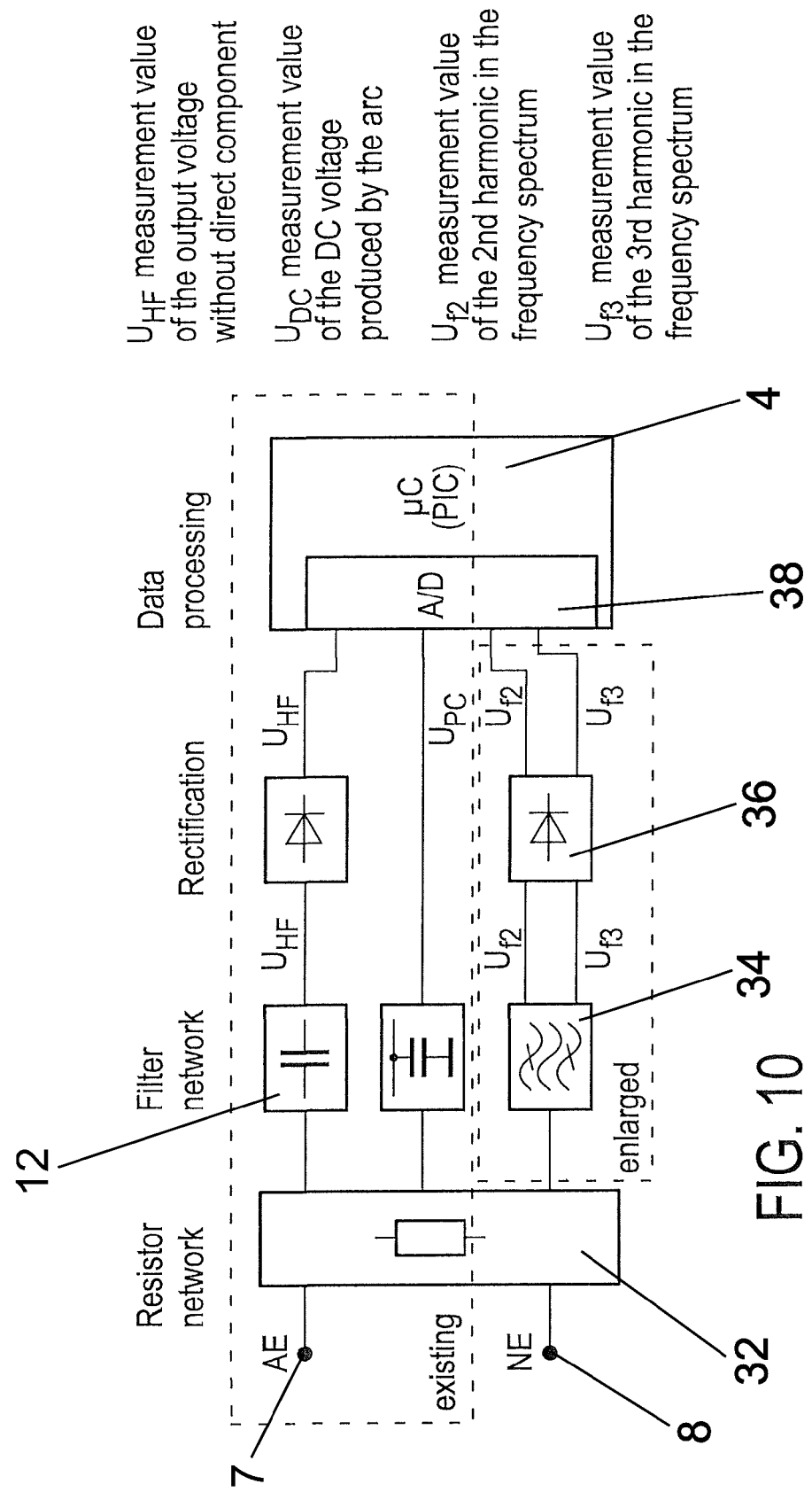
FIG. 10 shows a view in principle of an arc sensor according to the invention with integrated frequency spectrum evaluation.

The filter technology 34 according to the invention for evaluation of the frequency spectrum can be integrated into known HF surgery apparatuses 1, as is shown in FIG. 10.

The hardware and software was appropriately expanded for adaptation of frequency spectrum evaluation in the arc sensors 14 according to the invention. Upon expansion of the software for programming of the PIC microcontroller 4, consideration was given to processing additional measurement values. Data transfer to the CPU of the HF generator 2 was also adapted to the additional measurement values.

Results

The invention provides a novel measurement system for the detection of the arc parameters. The HF surgery apparatus 1 according to the invention embraces evaluation of the harmonics in the frequency spectrum of the output voltage of the HF generator 2. For expansion of arc regulation, the quotient of the DC voltage UDC and the amplitude of the second harmonic $\hat{u}f2$ from the frequency spectrum of the output voltage of the HF generator 2 was used to ascertain a parameter UDC/$\hat{u}f2$ with which the cutting speed is taken into account to a greater extent than in the case of previous HF surgery apparatuses 1 and thus that gives an improvement in the cutting result. Evaluating the amplitudes of the second and third harmonics $\hat{u}f2$ and $\hat{u}f3$ in the frequency spectrum of the output voltage of the HF generator 2, in conjunction with the DC voltage UDC, gave the parameter ($\hat{u}f2+\hat{u}f3$)/UDC with which it is possible to make a distinction between muscle tissue and fat tissue independently of the cutting speed. To enlarge the possible options for tissue differentiation, the combination with the also tissue-dependent parameter UHF/UDC (UHF=output voltage of the HF generator 2 without direct component) is further also proposed. The above-specified parameters for expanding the arc sensor system have been evaluated in extensive test series. The described design of suitable band pass filters 34 for the frequency ranges of 660-670 kHz and 990-1005 kHz illustrates an example of hardware implementation of harmonic evaluation.

Figure 11:
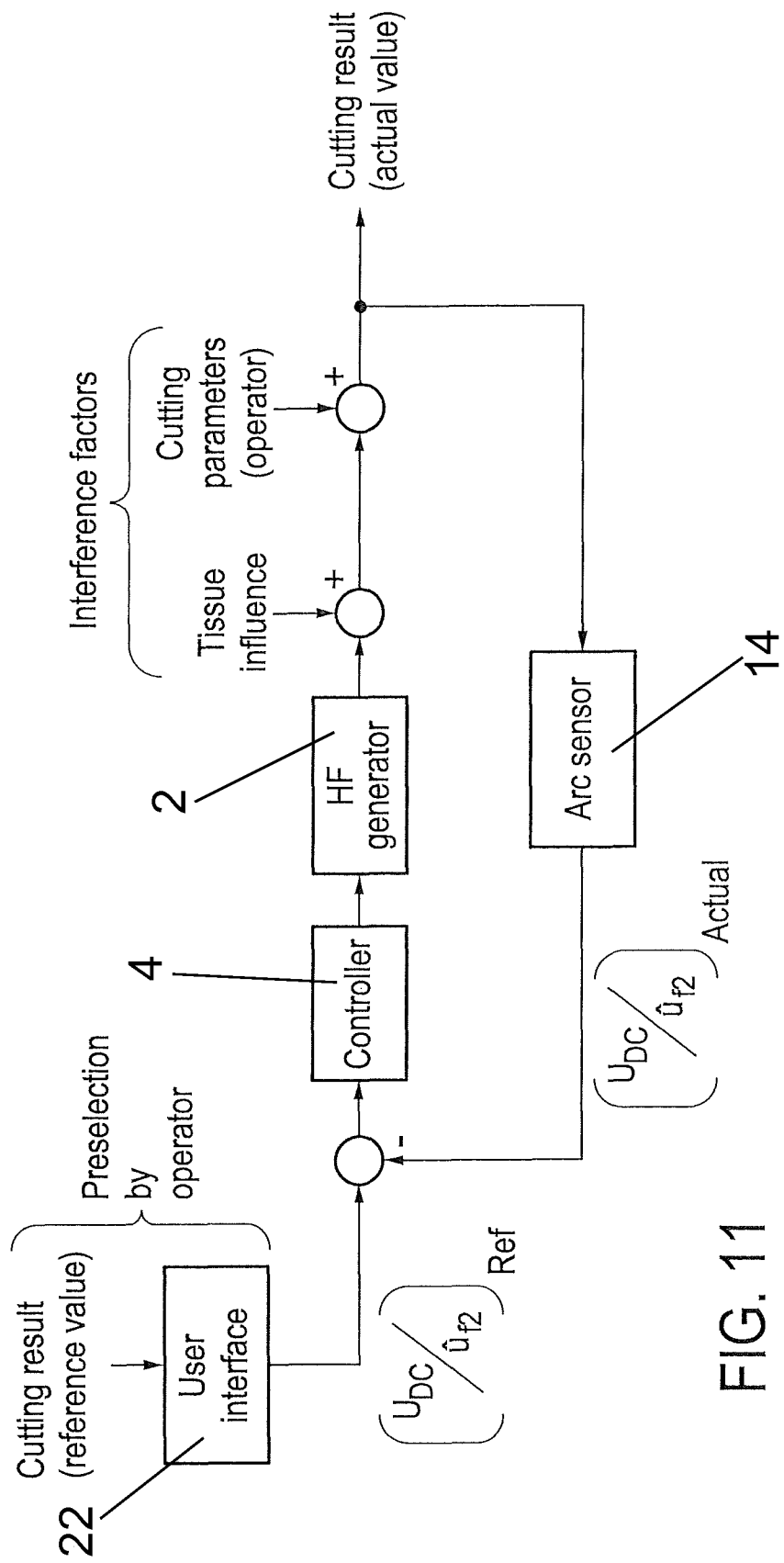
FIG. 11 shows a diagrammatic view of the operating principle of the arc regulation according to the invention (overall system)

The aim of the invention is to keep constant the degree of coagulation of the cut surfaces (cutting result) completely independently of tissue factors and the influencing parameters which are determined by the user such as cutting speed and cutting depth. Previous technical solutions for arc regulation take account in particular of the influence of tissue 5 on the cutting result. The invention describes arc regulation with which the cutting parameters can be more greatly taken into account. An HF surgery apparatus 1 according to the invention is shown in FIG. 11.

HF surgery apparatuses 1 and HF generators 2 of this invention, by virtue of the technical distinction between kinds of tissue 5, during the operational procedure, avoid unwanted injury or damage to surrounding pieces of tissue 5.

Figure 12:
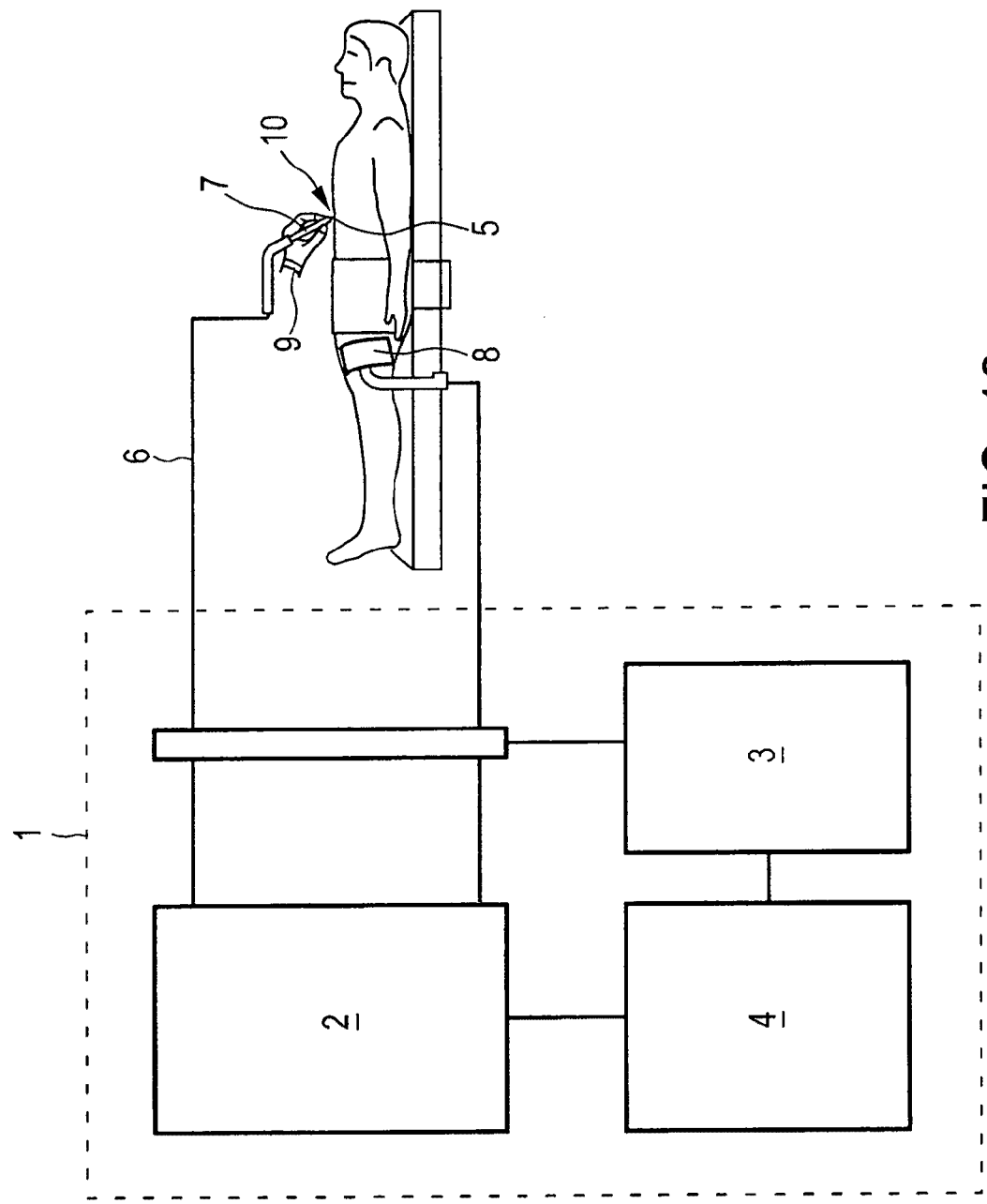
FIG. 12 shows a diagrammatic view of an embodiment by way of example of a high frequency surgery apparatus according to the invention.

FIG. 12 shows an embodiment of the HF surgery apparatus 1 according to the invention, with the HF generator 2, a measuring and calculating device 3 and a control device 4. An active electrode 7 and a neutral electrode 8 are connected to the HF generator 2. In operation the HF generator 2 forms a high frequency circuit 6, with the tissue 5 of a patient, that is to be treated. To cut the tissue 5 an operator 9 moves the active electrode 7 at a cutting speed, forming an arc 10. In that situation the measuring and calculating device 3, as described in detail hereinbefore, calculates the first and/or second tissue parameters and/or the speed parameter. In dependence on those parameters the measuring and calculating device 3 outputs a tissue signal and/or a speed signal to the control unit 4 which thus controls the output value of the HF generator 2.

The invention claimed is:

1. A high frequency surgery apparatus for cutting or coagulating biological tissue, comprising:
    at least one high frequency generator which in operation forms a high frequency circuit with the biological tissue with formation of an arc, and which produces an output voltage or an output current, and
    at least one measuring and calculating device which is connected to the high frequency circuit and which is configured: (a) to determine both a DC voltage in the high frequency circuit and amplitudes of at least one even and at least one odd harmonic of a fundamental frequency of the high frequency generator; and (b) to form a first tissue parameter representative of the biological tissue from a quotient of the sum of the amplitudes of the at least one even and the at least one odd harmonics to the DC voltage; and (c) to output a tissue signal dependent on the first tissue parameter for subsequent processing.

2. A high frequency surgery apparatus according to claim 1, including at least one control device connected for signal transmission to the measuring and calculating device and to the high frequency generator and configured to control or regulate an output value of the high frequency generator, wherein the control device is configured to control or regulate the output value based on of the tissue signal.

3. A high frequency surgery apparatus according to claim 1, wherein the measuring and regulating device is configured to determine the amplitudes of harmonics in the frequency spectrum of the output voltage or of the output current of the high frequency circuit.

4. A high frequency surgery apparatus according to claim 1, wherein the measuring and calculating device is configured to determine the amplitudes of second and third harmonics.

5. A high frequency surgery apparatus according to claim 1, wherein the measuring and calculating device is configured to measure the output voltage in the high frequency circuit and to form the first tissue parameter in dependence on the output voltage.

6. A high frequency surgery apparatus according to claim 1, wherein the measuring and calculating device is configured to form a second tissue parameter representative of the tissue to be treated from a relationship of the output voltage and the DC voltage in the high frequency circuit and to output the tissue signal in dependence on the first and second tissue parameters.

7. A high frequency surgery apparatus according to claim 1, wherein the measuring and calculating device is configured to determine both the DC voltage in the high frequency circuit and one of the output current in the high frequency circuit and the amplitude of the at least one harmonic of a fundamental frequency of the high frequency generator and to form a speed parameter representative of a cutting speed from one of: (a) a quotient of the DC voltage and the amplitude of the harmonic and (b) a quotient of the DC voltage and the output current and to output a speed signal dependent on the speed parameter for subsequent processing.

8. A high frequency surgery apparatus according to claim 2, wherein the measuring and regulating device is configured to determine the amplitudes of the harmonics in the frequency spectrum of the output voltage or of the output current of the high frequency circuit.

9. A high frequency surgery apparatus for cutting biological tissue, comprising:
    a high frequency generator which in operation forms a high frequency circuit with the biological tissue with formation of an arc, and which produces an output voltage or an output current,
    at least one measuring and calculating device which is connected for signal transmission to the high frequency circuit and which is configured to determine both a DC voltage in the high frequency circuit and one of (a) the output current in the high frequency circuit and (b) an amplitude of at least one harmonic of a fundamental frequency of the high frequency generator;
    wherein said measuring and calculating device being also configured to form a speed parameter representative of a cutting speed from one of: (a) a quotient of the DC voltage and the amplitude of the harmonic and (b) a quotient of the DC voltage and the output current; and
    said measuring and calculating device being also configured to output a speed signal dependent on the speed parameter for subsequent processing.

10. A high frequency surgery apparatus according to claim 9, including at least one control device connected to the measuring and calculating device for controlling or regulating the output value of the high frequency generator, wherein the control device is configured to control or regulate the output value based on the speed signal.

11. A high frequency surgery apparatus according to claim 9, wherein the measuring and regulating device is configured to determine the amplitude of the harmonics or of the output current of the high frequency circuit.

12. A high frequency surgery apparatus according to claim 9, wherein the measuring and calculating device is configured to determine the amplitude of an even, second harmonic of the high frequency generator.

13. A high frequency surgery apparatus according to claim 10, wherein the measuring and regulating device is configured to determine the amplitude of the harmonics in the frequency spectrum of the output voltage or of the output current of the high frequency circuit.

14. A high frequency surgery method, comprising:
    cutting and/or coagulating biological tissue with a high frequency circuit formed between at least one high frequency generator and the biological tissue, with the formation of an arc, determining both a DC voltage in the high frequency circuit and amplitudes of at least one even and at least one odd harmonic of a fundamental frequency of the high frequency generator, determining a first tissue parameter representative of the biological tissue from a quotient of the sum of the amplitudes of the at least one even and the at least one odd harmonics to the DC voltage; and outputting a tissue signal dependent on the first tissue parameter for subsequent processing.

15. A method according to claim 14, including controlling an output value of the high frequency generator in dependence on the tissue signal.

16. A high frequency surgery method, comprising:

cutting and/or coagulating biological tissue with a high frequency circuit formed between at least one high frequency generator and the biological tissue, with the formation of an arc, determining both a DC voltage in the high frequency circuit and also an effective value of an output current in the high frequency circuit or the amplitude of at least one harmonic of a fundamental frequency of the high frequency generator, determining a speed parameter representative of a cutting speed from the quotient of the DC voltage and the amplitude of the at least one harmonic or the quotient of the DC voltage and the output current, and outputting a speed signal dependent on the speed parameter for subsequent processing.

17. A method according to claim 16, including controlling an output value of the high frequency generator in dependence on the tissue signal.

\* \* \* \* \*